US006413571B1

(12) United States Patent
Liu

(10) Patent No.: US 6,413,571 B1
(45) Date of Patent: Jul. 2, 2002

(54) STEROL ESTERS OF CONJUGATED LINOLEIC ACIDS AND PROCESS FOR THEIR PRODUCTION

(75) Inventor: Linsen Liu, Irvine, CA (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 09/693,562

(22) Filed: Oct. 20, 2000

Related U.S. Application Data
(60) Provisional application No. 60/160,894, filed on Oct. 21, 1999.

(51) Int. Cl.[7] .............................................. A23D 9/007
(52) U.S. Cl. ....................... 426/611; 552/544; 552/547; 552/554; 554/174
(58) Field of Search .................... 426/611; 552/544, 552/545, 547, 554; 514/170, 171, 182, 562; 554/174; 435/134, 135

(56) References Cited

U.S. PATENT DOCUMENTS

| | | | |
|---|---|---|---|
| 5,502,045 A | | 3/1996 | Miettinen et al. |
| 5,554,646 A | | 9/1996 | Cook et al. |
| 5,760,082 A | | 6/1998 | Cook et al. |
| 5,892,068 A | | 4/1999 | Higgins, III |
| 5,919,451 A | | 7/1999 | Cook et al. |
| 6,031,118 A | * | 2/2000 | van Amerongen et al. . 552/544 |
| 6,106,886 A | * | 8/2000 | van Amerongen et al. . 426/611 |
| 6,123,979 A | * | 9/2000 | Hepburn et al. ............ 426/611 |
| 6,139,897 A | * | 10/2000 | Goto et al. .................. 426/601 |
| 6,147,236 A | * | 11/2000 | Higgins, III. ................ 552/554 |
| 6,231,915 B1 | * | 5/2001 | van Amerongen et al. . 426/611 |
| 2002/0010349 A1 | * | 1/2002 | Roden |

FOREIGN PATENT DOCUMENTS

| | | | | |
|---|---|---|---|---|
| DE | 197 50 422 C 1 | | 11/1998 | .............. C07J/9/00 |
| EP | 0 982 316 A | | 3/2000 | .............. C07J/9/00 |
| WO | WO98/38206 | * | 9/1998 | |
| WO | WO 99/56558 | | 11/1999 | |

OTHER PUBLICATIONS

J. Agricultural and Food Chem 49(11)5210–5216.*
Abstract from DATABASE BIOSIS Online!. BIO-SCIENCES INFORMATION Service, Philadelphia, PA, US; May 1999 (1999–05); Gylling Helena et al: "Cholesterol reduction by different plant stanol mixtures and with variable fat intake." Database accession No. PREV199900281083 XP002167425 abstracted from Metabolism Clinical and Experimental, vol. 48, No. 5 May 1999, pp. 575–580. ISSN: 0026–0495.

Abstract from DATABASE CHEMABS Online!. Chemical Abstracts Service, Columbus, OH, US; Kaoru, Kazuhisa et al: "Conjugated linoleic acid esters as antioxidants, their manufacture, and antioxidants and food containing the esters" retrieved from STN Database accession No. 133:221697 XP002167426 abstracted from JP 2000 247965 A, (Snow Brand Milk Products Co., Ltd., Japan) Sept. 12, 2000.

Abstract of Dyas, L. et al.: "Steryl fatty acyl esters in plants", *Phytochemistry*, Sept. 1993, v. 34(1) pp. 17–29.

Abstract of Field, F. et al.: "Effect of micellar beta–sitosterol on cholesterol metabolism in CaCo–2 cells", *Journal of Lipid Research*, Feb. 1997, v. 38(2) pp. 348–360.

Abstract of Gylling, H. Siimes, et al.: "Sitostanol ester margarine in dietary treatment of children with familial hypercholesterolemia", *Journal of Lipid Research*, Aug. 1995, v. 36(8) pp. 1807–1812.

Abstract of Micich, T.J. et al.: "Polymer–supported saponins: an approach to cholesterol removal from butteroil", *Journal of Agricultural and Food Chemistry*, Aug. 1992, v. 40 (8) pp. 1321–1325.

Haumann, Barbara F.: "Conjugated linoleic acid offers research promise", *Inform*, 1996, pp. 152–153, 156–159, vol. 7, No. 2.

O'Shea, M. et al.: "Conjugated linoleic acid in bovine milk fat: a food–based approach to cancer chemoprevention", *Trends in Food Science & Technology*, 1998, pp. 192–196, vol. 9, Elsevier Science Ltd.

"Phytosterols", *Critical Reviews in Food Science and Nutrition*, 1999, pp. 275–283, vol. 39, No. 3, CRC Press LLC.

Steinhart, Carol: "Conjugated Linoleic Acid the Good News about Animal Fat", *Journal of Chemical Education*, 1996, p. A302, vol. 73, No. 12.

* cited by examiner

*Primary Examiner*—Carolyn Paden
(74) *Attorney, Agent, or Firm*—Fellers, Snider, Blankenship, Bailey & Tippens, P.C.

(57) ABSTRACT

Novel sterol/stanol esters of a conjugated fatty acid are provided through the esterification or transesterification of a sterol such as beta-sitosterol or a hydrogenated form thereof (stanol). Such novel esters exhibit the combined properties normally possess by the sterol/stanol compound and the conjugated fatty acid and as such are excellent additives for dietetic foods and supplements.

10 Claims, No Drawings

STEROL ESTERS OF CONJUGATED LINOLEIC ACIDS AND PROCESS FOR THEIR PRODUCTION

CROSS REFERENCE TO RELATED APPLICATION

This application claims the benefit of my copending U.S. provisional application Serial No. 60/160,894, filed Oct. 21, 1999.

BACKGROUND OF THE INVENTION

1. Technical Field

This invention relates to novel sterol esters of conjugated linoleic acids and a process for the production of the same by esterification of sterols and stanols with a conjugated linoleic acid.

2. Background

It is known that the addition of plant sterol (phytosterol) to diets will reduce serum cholesterol levels. Such additives effect the reduction of serum cholesterol through the disruption of intestinal absorption of dietary cholesterol by displacing it from bile and micelli. Free sterols or stanols, though, are not optimum candidates for use in typical pharmaceutical or dietary dosage forms as cholesterol reducing agents due to their very high melting points 130 C. and low solubility in aqueous and oil media. As a result such compounds are preferred to be converted into their fatty esters for food applications, which reduce their melting points and solubility in oil. However, the fatty acids attached to sterol in the current commercial products are from vegetable oil such as sunflower, canola, or soybean oil. Those fatty acids provide no pharmaceutical or nutraceutical functions except increasing the total calories of the products.

Conjugated fatty acids are known to have many health benefits such as reducing body fat, inhibiting tumor growth and reducing atherosclerosis. Such conjugated fatty acids are naturally found in beef and dairy fats in trace amounts (0.2–30 mg/g food). One such conjugated fatty acid is conjugated linoleic acid (octadecadienoic acid), hereinafter referred to as CLA. Cattle convert the linoleic acid in grass into CLA by their special digestive processes. However, since humans cannot produce such conjugated fatty acids, such additives to the human system must be through the diet. Thus the providing of CLA in a form to permit its use in dietetic foods would serve as a significant contribution to the field of dietetic foods since it would enable the recipient to receive a valuable additive since it is known that CLA is effective in increasing body protein or preventing the loss of body protein in a human, increasing food efficiency in humans and assists in reducing body fat.

It is thus an object of the present invention to provide a novel ester composition consisting essentially of phytosterols including plant sterols/stanols and conjugated linoleic acids.

Another object of this invention is to prepare sterol and stanol esters of CLA for their utilization in food and dietary supplement products.

Another object of the present invention is to provide a process for the production of sterol esters of conjugated linoleic acids through transesterification and/or esterification.

SUMMARY OF THE INVENTION

In accordance with one embodiment of the present invention, I have discovered that through the esterification of a sterol or stanol with a conjugated fatty acid, such as CLA, there is provided a compound which provides the advantages of both the conjugated fatty acid and the sterol or stanol. CLA is a liquid fatty acid with two conjugated double bonds, therefore, it can reduce the melting point of sterols and stanols dramatically. Indeed, the beta-sitosterol ester of CLA is liquid at ambient temperature while the current commercial products made of the fatty acids derived from vegetable oils are solid or semisolid. The sterol ester of CLA also provides a product having lower total calories than the blended product that provides the same doses of sterol and CLA. Such new products thus offer the combined benefits of sterols/stanols as a cholesterol control agent and CLA as an anticarcinogen and fat reducing agent. Such esters can be used as a supplement or ingredient in foods.

In accordance with another embodiment of the present, sterol esters can be readily prepared through esterification of sterol or stanol with the conjugated fatty acid or by transesterification of sterol or stanol with of the conjugated fatty acid methyl ester. Transesterification is the preferred method to those skilled in the art.

A better understanding of the present invention, its several aspects, and its advantages will become apparent to those skilled in the art from the following detailed description, wherein there is shown and described the preferred embodiment of the invention, simply by way of illustration of the best mode contemplated for carrying out the invention.

DETAILED DESCRIPTION OF THE PREFERRED EMBODIMENT

As used herein the term "sterol ester" includes both the plant sterol ester per se as well as the hydrogenated sterol products which are referred to as stanol and campestanol. Such compounds have the following general formula:

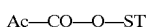

wherein Ac—CO is an acyl group from a conjugated fatty acid and O—ST is a steryl group derived from a sterol/stanol.

The term "conjugated fatty acid" is intended to refer to conjugated linoleic acid (CLA) which in turn refers to a group of geometrical and positional isomers of linoleic acids including but not limited to 9,11-octadecadienoic acid, and 10–12 octadecadienoic acid. The cis-9, trans-11 isomer is the most dominant isomer of CLA in dairy products and is also the most biologically active form as known at present.

The term "sterol" or "sterol/stanol" as used herein is intended to mean the sterol compound per se or its hydrogenated form including stanol and campestanol.

The present invention is based upon my discovery that through the use of the conjugated fatty acid—CLA—in the esterification of a sterol there is obtained a product which is liquid at ambient temperature and which product has lower total calories and which product provides the combined benefits of cholesterol control agent and an anticarcinogen and fat reducing agent.

The present invention provides a process for esterfying stanols or/and sterols with CLA. This esterification reaction may be accomplished either through the reaction of the sterol with CLA using a esterification catalyst such as sulphonic acids and tin chloride or though the reaction of the sterol with CLA methyl ester using a transesterification catalyst such as sodium methoxide and hydroxide. The results of those esterification reactions is a sterol ester of CLA or a stanol ester of CLA.

While any stanol or sterol that is functionalized with a hydroxy group is suitable for transesterification and esterification by the processes as described herein, in one presently preferred embodiment of the present invention there is utilized a sterol/stanol selected form the group consisting of beta-sitosterol, campesterol, stigmasterol and sitostanol. Other suitable sterols include but not limited to brassicasterol, avenasterol, alpha-spinasterol and ergosterol. It is understood that those sterols/stanols for esterifying may be used in pure form or mixed in certain ratios.

Likewise while any isomer of a conjugated linoleic acid is suitable for esterification by the process as described herein, in one presently preferred embodiment of the present invention there is utilized a conjugated linoleic acid selected from the group consisting of cis-9, trans-11-conjugated linoleic acid and trans-10, cis 12-conjugated linoleic acid.

The acid-catalyzed esterification reaction of sterol with CLA and base-catalyzed transesterification reaction of sterol with CLA methyl ester, respectively, are depicted below demonstrating the formation of a sterol ester of CLA per the present invention. As shown in the reaction mechanism on the left sterol is reacted with CLA in the presence of an acid catalyst to produce sterol ester of CLA. In the reaction mechanism on the right (which represents the preferred mechanism), sterol is reacted with CLA methyl ester to produce sterol ester of CLA in the presence of a base catalyst.

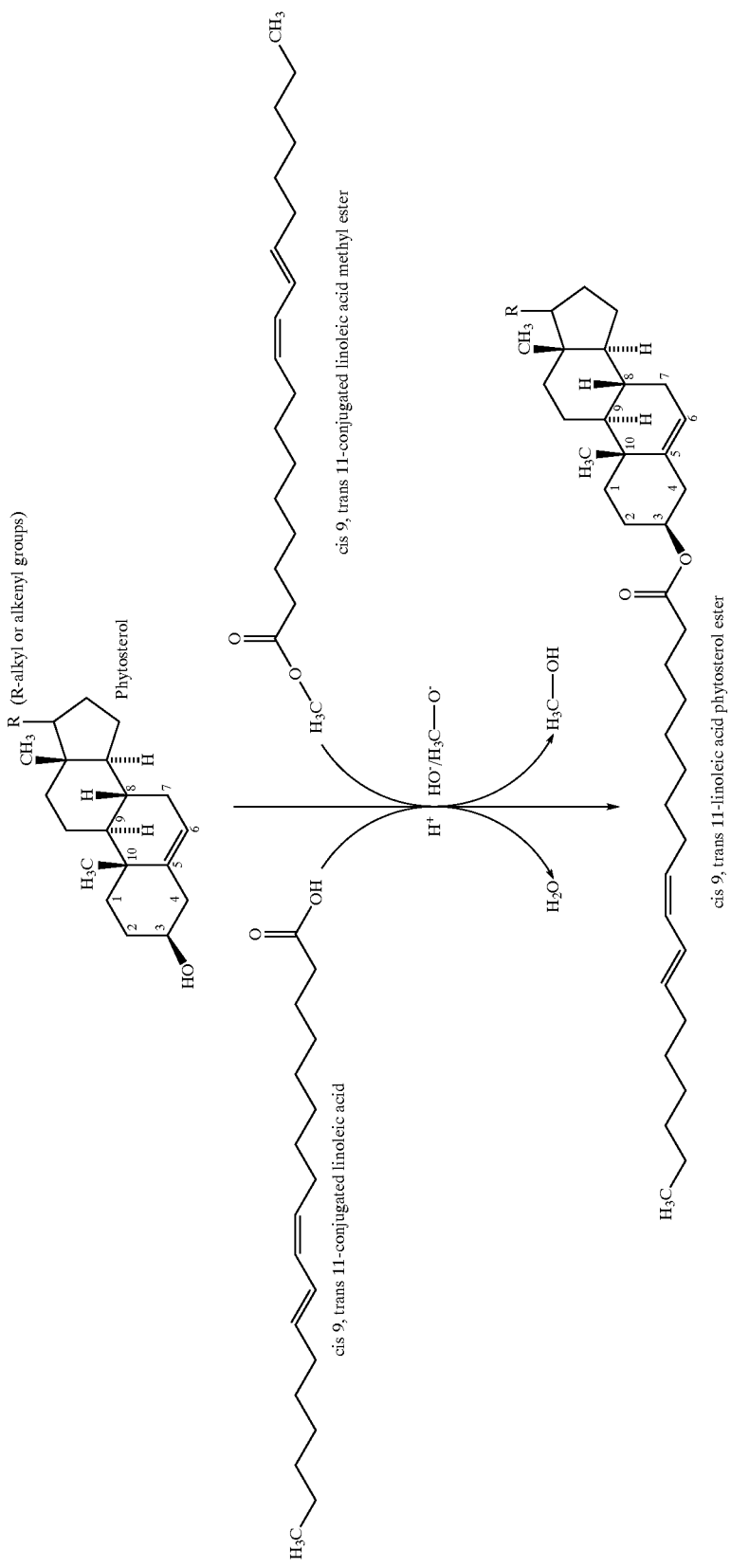

R is defined as following alkyl or alkenyl groups:
- beta-Sitosterol: —CH(CH3)CH2CH2CH(C2H5)CH(CH3)2
- Stigmasterol: —CH(CH3)CH=CHCH(C2H5)CH(CH3)2
- Campesterol: —CH(CH3)CH=CHCH(CH3)CH(CH3)2 (no double bond at 5, 6)
- Brassicasterol: —CH(CH3)CH=CHCH2CH(CH3)2
- Avenasterol: —CH(CH3)CH2CH2C(=CH—CH3)CH(CH3)2 (double bond at 5, 6 or 7, 8 only)
- alpha-Spinasterol: —CH(CH3)CH=CHCH2C(C2H5)CH(CH3)2(double bond at 7, 8)
- Ergosterol: —CH(CH3)CH=CHCH(CH3)CH(CH3)2 (double bonds at 5, 6 and 7, 8)

A similar reaction system is carried out when the hydrogenated sterol such as stanol is the reactant.

The molar ratios of the starting materials for the transesterification and esterification reactions are provided in stoichiometric levels. It is preferred that the CLA be present in at least 5–10% excess so as to react with all of the sterol or stanol. Any excess unreacted CLA is easily removed in the product work-up.

The usage of esterification catalyst varies with the catalyst used and their uses are reviewed in Bailey's Industrial Oil and Fat Products, 4th edition, edited by Daniel Swern, Volume 2, PP 113–127. Since esterification involves high reaction temperature and low reaction rate, sterol ester of CLA are preferred to be prepared via transesterification.

In carrying out the process of the present invention solvents such as ethers and short chain alkanes may be added to the reaction mixture to promote reaction.

The reaction rate of transesterification increases at an elevated temperature. The typical reaction temperature ranges from 40 C. to about 250 C. The reaction period may vary widely, but as a general practice a reaction time in the range of about 4 to about 20 hours can be utilized. The reaction is normally carried out for a time which will permit the reaction to go to completion so that the sterol or stanol present is completly esterified. Normally the ester product is obtained in yields of greater than 95%.

Following completing of the reactions, the resulting ester product can be isolated with or without organic solvent extraction after removing the catalyst such as by water washing. Typical solvents are low boiling point organic compounds including but not limited to diethyl or petroleum ethers, hexane, dichloromethane, chloroform, and toluene.

The following examples are intended to be illustrative of the present invention and to teach one of ordinary skill in the art to make and use the invention. These examples are not intended to limit the invention in any way.

EXAMPLE 1

To Prepare Sterol Esters from Conjugated Linoleic Acid Methyl Ester

A commercial CLA methyl ester product was used in the synthesis, which contains 41% of cis 9, trans 11, 44% of trans 10, cis 12, and 10% of cis 10, cis 12 conjugated linoleic acids. 60 grams of plant sterols containing 40% beta-sitosterol, 20–30% campesterol and 10–30% dihydrobrassicasterol was mixed with 100 grams of CLA methyl ester. The mixture is solid at room temperature. After dried at 90–105 C. under about 20 mm Hg vacuum for about an hour, the mixture was cooled down to about 70 C., and 1.3 grams of 25% NaOCH3-Methanol solution was added. A vacuum of up to 20 mm Hg was applied slowly to remove the methanol produced. When no vigorous bubbles came out, the reaction was continued under a high vacuum up to 0.01 mm Hg and the temperature was raised gradually to 110 C. The reaction continued until no methanol was bubbling, then the mixture was cooled down to about 60 C. before breaking the vacuum with $N_2$. 6 grams of warm water (40–50 C.) was added to destroy the catalyst. The mixture was stirred for about 1 minute until appearing homogenous and then centrifuged at 5000 G for 5 minutes. The top layer containing sterol esters was collected and washed with 12 g warm water. The mixture was then centrifuged to recover the top sterol ester layer. The sterol ester was then purified by vacuum distillation to remove moisture and residual methyl esters. The product is liquid at ambient temperature and has three melting peaks at 15, 37, and 58 C. as measured by DSC.

EXAMPLE 2

To Prepare Sterol Esters from Conjugated Linoleic Acid

CLA One™, a commercial CLA product available from Pharmanutrients, Inc. and which contains 75% of free fatty acid, was used in this synthesis. CLA One™ typically contains with 35% cis 9, trans 11 and 36% trans 10, cis 12-linoleic acids. 150 g of CLA One™ was mixed with 600 mL methanol and 12 mL concentrated sulfuric acid. The mixture was refluxed for 30 minutes to prepare the methyl esters of fatty acids. The product was washed twice with 100 mL 5% sodium chloride and with 2% potassium bicarbonate until nutral pH in the aqueous phase. The methyl esters of fatty acids were dried by heating at 90–105 C. under up to 20 mm Hg vacuum. One hundred grams of methyl ester produced as above was mixed with 60 g plant sterols that contains 40% beta-sitosterol, 20–30% campesterol and 10–30% dihydrobrassicasterol. The mixture was dried at 90–105 C. under up to 20 mm Hg vacuum for about an hour. After cooling the mixture down below 70 C., 0.5 grams of NaOCH3 powder was added to the reactant mixture as transesterification catalyst. Vacuum was applied slowly to remove the methanol produced so the reaction proceeded to the direction forming sterol esters. When vigorous bubbling ceased, the reaction was continued under a high vacuum up to 0.01 mm Hg and the temperature was raised gradually to 110 C. The reaction continued until no methanol was bubbling out. The mixture was cooled down to about 60 C. and nitrogen was introduced to break the vacuum. 6 grams of 50% citric acid aqueous solution was added to neutralize the transesterification catalyst. The mixture was stirred for about 6 minutes or until appearing homogenous and then centrifuged at 4000 G for 5–30 minutes. The top layer containing sterol esters was collected and washed twice with 12 g warm water. The mixture was then centrifuged at 4000 G for 5 minutes to recover the top sterol ester layer. The sterol ester was then purified by vacuum distillation to remove moisture and residual methyl esters.

The specific examples herein disclosed are to be considered as being primarily illustrative. Various changes beyond those described will not doubt occur to those skilled in the art and such changes are to be understood as forming a part of this invention insofar as they fall within the spirit and scope of the appended claims.

The inventive compositions are usable as a component in any number of food products or as a dietary supplement whereby the compositions may be delivered in a convenient form and the advantages thereof may be easily obtained.

What is claimed is:

1. A process for the production of sterol or stanol esters of a conjugated linoleic acid which comprises reacting under conditions suitable for effecting transesterification an alcohol ester of a conjugated linoleic acid and a sterol or stanol in the presence of a transesterification catalyst.

2. A process in accordance with claim 1 wherein said conjugated linoleic acid is selected from the group consisting of cis-9, trans-11-conjugated linoleic acid and trans-10, cis-12-conjugated linoleic acid.

3. A process in accordance with claim 2 wherein said conjugated linoleic acid is cis-9, trans-11 conjugated linoleic acid.

4. A process in accordance with claim 3 wherein said conjugated linoleic acid is trans-10, cis-12-conjugated linoleic acid.

5. A process in accordance with claim 1 wherein said sterol is selected from the group consisting of beta-sitosterol, campesterol, stigmasterol, sitostanol, and campestanol.

6. A process in accordance with claim 5 wherein said sterol is beta-sitosterol.

7. A process in accordance with claim 5 wherein said sterol is campesterol.

8. A process in accordance with claim 5 wherein said sterol is stigmasterol.

9. A process in accordance with claim 5 wherein said sterol is sitostanol.

10. A process in accordance with claim 5 wherein said sterol is campestanol.

* * * * *